United States Patent [19]
Dao et al.

[11] Patent Number: 5,749,727
[45] Date of Patent: May 12, 1998

[54] TRANSDUCER ACTIVATED SUBGINGIVAL TOOL TIP

[75] Inventors: Huy-Can Dao, North Brunswick, N.J.; George H. Warrin, North Merrick, N.Y.; Harvey B. Foulkes, Commack, N.Y.; Rene Perdreaux, Brooklyn, N.Y.; Edward W. Lee, Bethpage, N.Y.

[73] Assignee: Dentsply Research & Development Corp., Milford, Del.

[21] Appl. No.: 635,083

[22] Filed: Apr. 19, 1996

Related U.S. Application Data

[63] Continuation-in-part of Ser. No. 268,418, Aug. 26, 1994, Pat. No. 5,531,597, which is a continuation-in-part of PCT/US95/08363 Jun. 27, 1995.

[60] Provisional application No. 60/011,072, Feb. 2, 1996, and provisional application No. 60/010,933, Jan. 31, 1996.

[51] Int. Cl.$^6$ .................. A61C 1/07; A61C 3/03; A61C 3/08

[52] U.S. Cl. .................. 433/119; 433/216; 433/166; 433/86

[58] Field of Search .................. 433/82, 86, 118, 433/119, 125, 165, 166, 215, 216

[56] References Cited

U.S. PATENT DOCUMENTS

| | | | |
|---|---|---|---|
| D. 261,932 | 11/1981 | Bussiere | D24/10 |
| 2,921,372 | 1/1960 | Bodine, Jr. | 32/27 |
| 3,076,904 | 2/1963 | Kleesattel et al. | 310/26 |
| 3,124,878 | 3/1964 | Bodine, Jr. et al. | 32/26 |
| 3,368,280 | 2/1968 | Friedman et al. | 32/58 |
| 3,488,851 | 1/1970 | Haydu | 32/58 |
| 3,518,766 | 7/1970 | Burt | 32/58 |
| 3,589,012 | 6/1971 | Richman | 32/58 |
| 3,593,425 | 7/1971 | Robinson | 32/58 |
| 3,645,255 | 2/1972 | Robinson | 128/24 A |
| 3,654,502 | 4/1972 | Carmona et al. | 310/26 |
| 3,703,037 | 11/1972 | Robinson | 32/58 |
| 3,924,335 | 12/1975 | Balamuth et al. | 32/58 |
| 3,930,173 | 12/1975 | Banko | 310/26 |
| 3,956,826 | 5/1976 | Perdreaux, Jr. | 32/58 |
| 4,038,571 | 6/1977 | Hellenkamp | 310/8.2 |
| 4,048,723 | 9/1977 | Thorup | 32/40 |
| 4,110,908 | 9/1978 | Cranston | 32/50 |
| 4,168,447 | 9/1979 | Bussiere et al. | 310/316 |

(List continued on next page.)

FOREIGN PATENT DOCUMENTS

| | | |
|---|---|---|
| 0 261 272 | 3/1988 | European Pat. Off. |
| 2143251 | 2/1973 | France. |
| 2566262 | 6/1984 | France. |
| 2550439 | 2/1985 | France. |
| 3 032 022 | 3/1982 | Germany. |
| 2 550 441 | 2/1985 | Germany. |
| 33 28 605 | 2/1985 | Germany. |
| 2 637 176 | 4/1990 | Germany. |
| 1-212547 | 8/1989 | Japan. |

OTHER PUBLICATIONS

Unisonic Transistorized Ultrasonic Scaler.Precision Research Corp. (1968).

The Dentsply–Cavitron Powermatic Ultrasonic Dental Unit. Dentsply International (1976).

*Primary Examiner*—Nicholas D. Lucchesi
*Attorney, Agent, or Firm*—Dale R. Lovercheck; James B. Bieber

[57] ABSTRACT

A transducer activated subgingival tool for contacting subgingival tooth surfaces and directing a fluid adjacent to said surfaces, wherein the tool has an activated tip having a fluid inlet end, a subgingival outlet end, a step in the surface of the outer wall of said tip between said inlet end and said subgingival outlet end, and a fluid passageway wall internal to the tip. The passageway wall is formed in the inlet end generally along the longitudinal center axis of the inlet end of the tip. In a preferred embodiment of the invention, the step intersects the passageway wall at the orifice edge.

42 Claims, 12 Drawing Sheets

U.S. PATENT DOCUMENTS

| | | | |
|---|---|---|---|
| 4,169,984 | 10/1979 | Parisi | 310/323 |
| 4,260,380 | 4/1981 | Nash | 433/119 |
| 4,276,880 | 7/1981 | Malmin | 128/221 |
| 4,283,175 | 8/1981 | Nash | 433/119 |
| 4,315,742 | 2/1982 | Nash et al. | 433/86 |
| 4,332,558 | 6/1982 | Lustig | 433/86 |
| 4,370,131 | 1/1983 | Banko | 443/86 |
| 4,427,384 | 1/1984 | Serlich | 433/120 |
| 4,453,919 | 6/1984 | Takeshita | 433/120 |
| 4,578,033 | 3/1986 | Mossle et al. | 433/29 |
| 4,589,847 | 5/1986 | Loge et al. | 433/126 |
| 4,634,376 | 1/1987 | Mossle et al. | 433/29 |
| 4,820,152 | 4/1989 | Warrin et al. | 433/86 |
| 5,082,443 | 1/1992 | Lohn | 433/80 |
| 5,125,837 | 6/1992 | Warrin et al. | 433/98 |
| 5,190,456 | 3/1993 | Hasegawa | 433/120 |
| 5,531,597 | 7/1996 | Foulkes et al. | 433/119 |
| 5,567,153 | 10/1996 | Foulkes et al. | 433/119 |

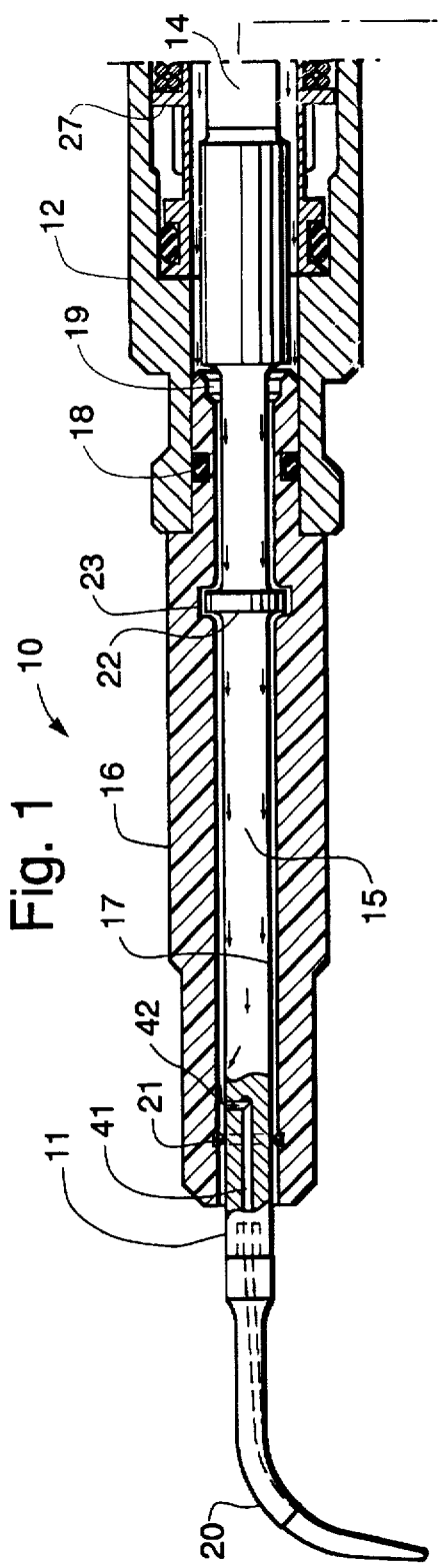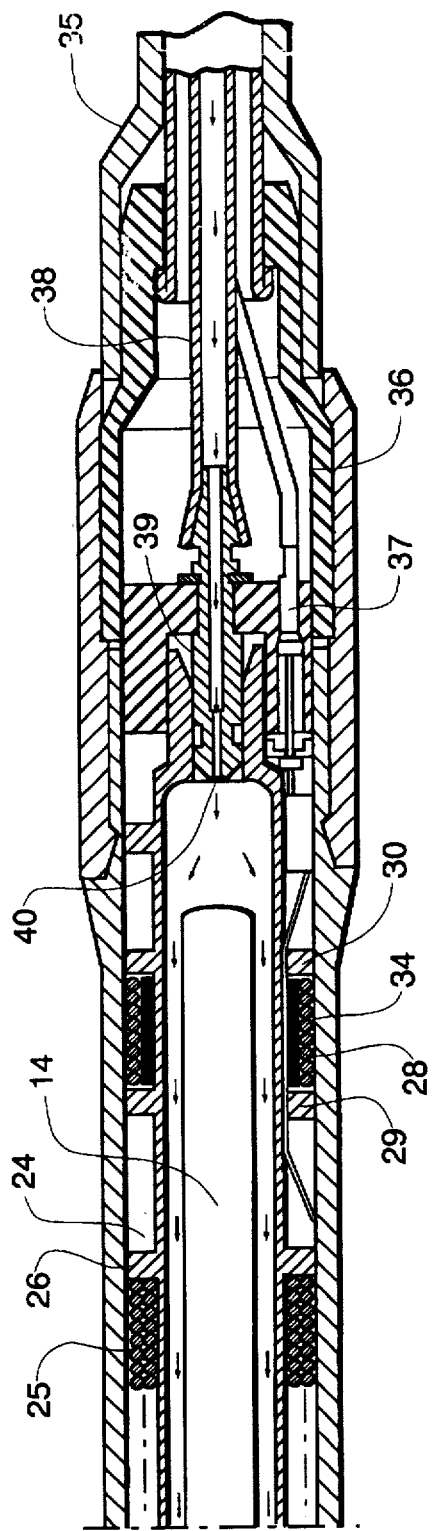
Fig. 1

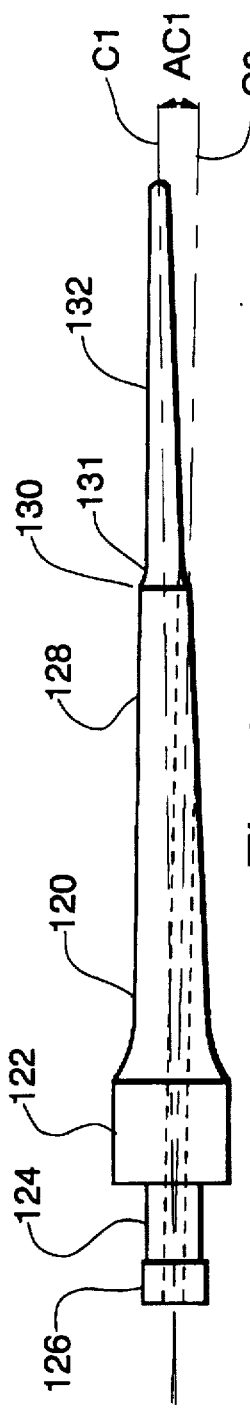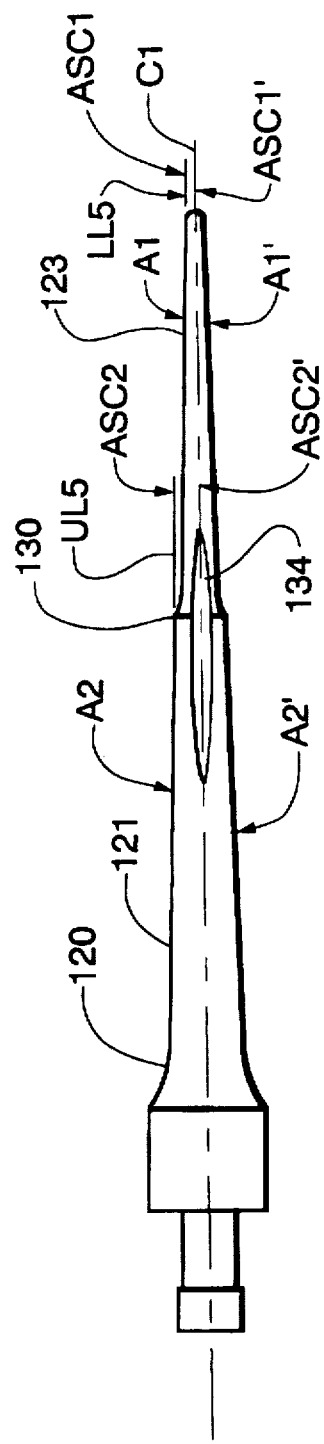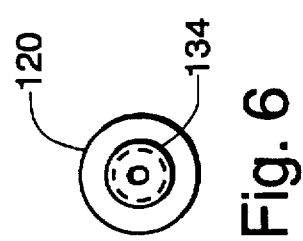

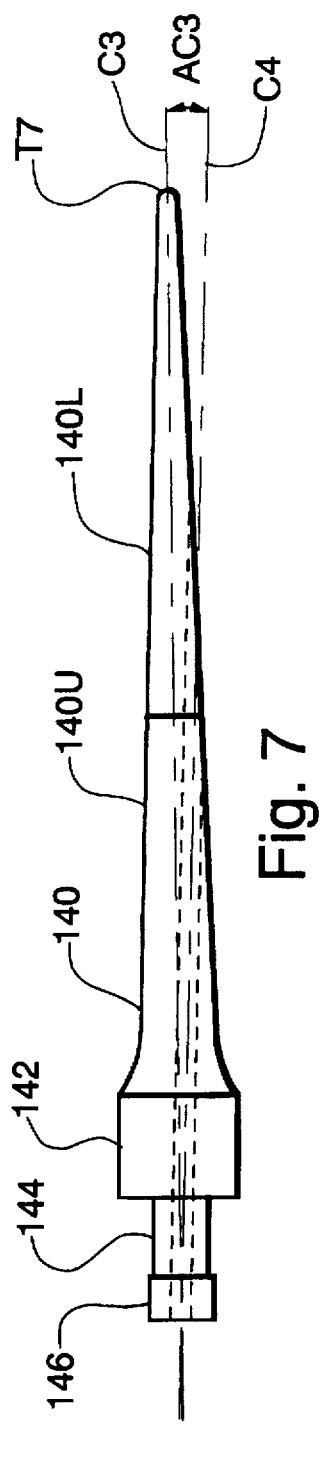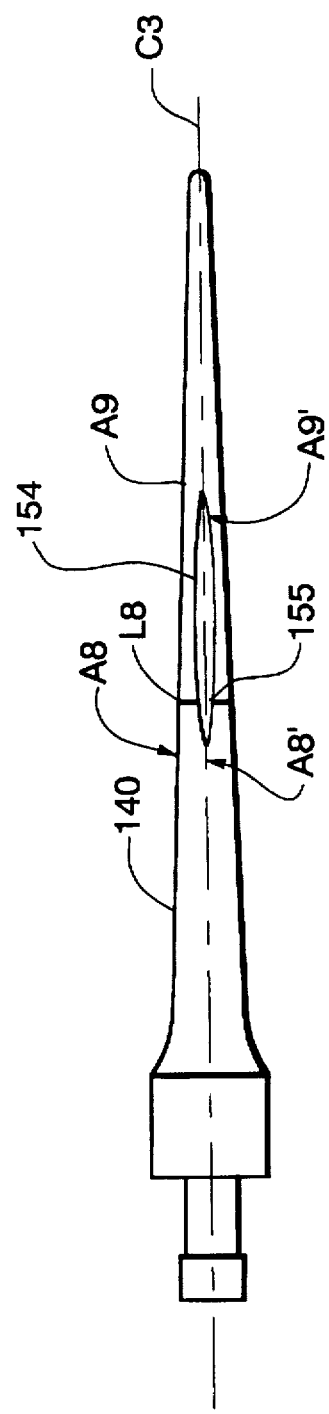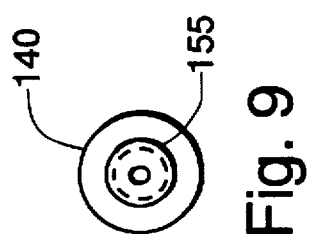

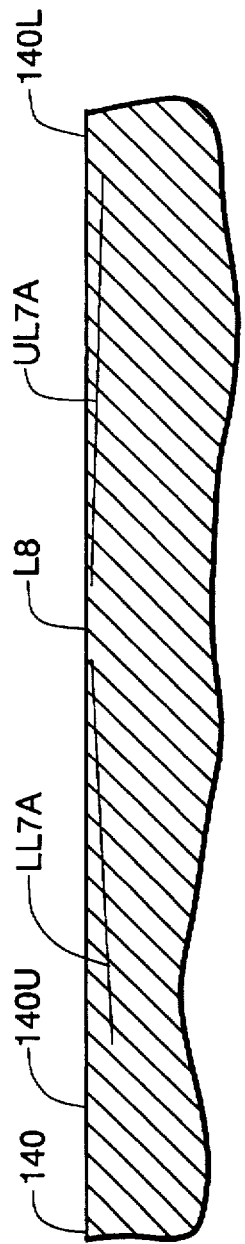
Fig. 7A
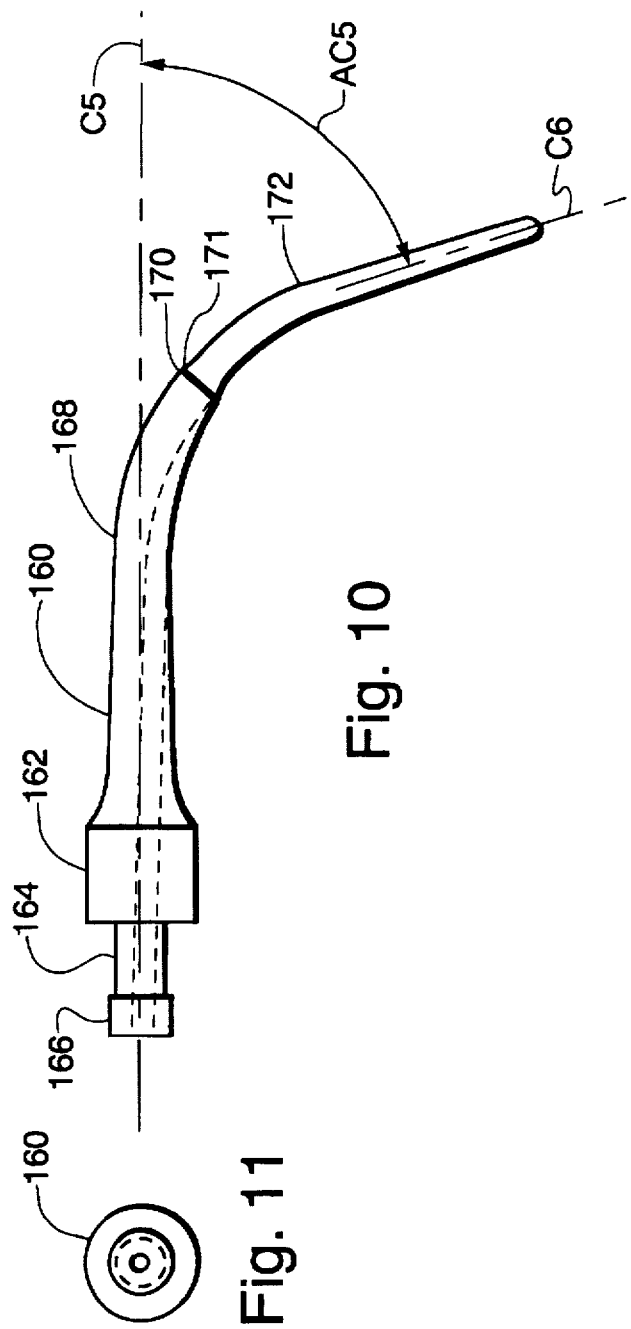
Fig. 10
Fig. 11

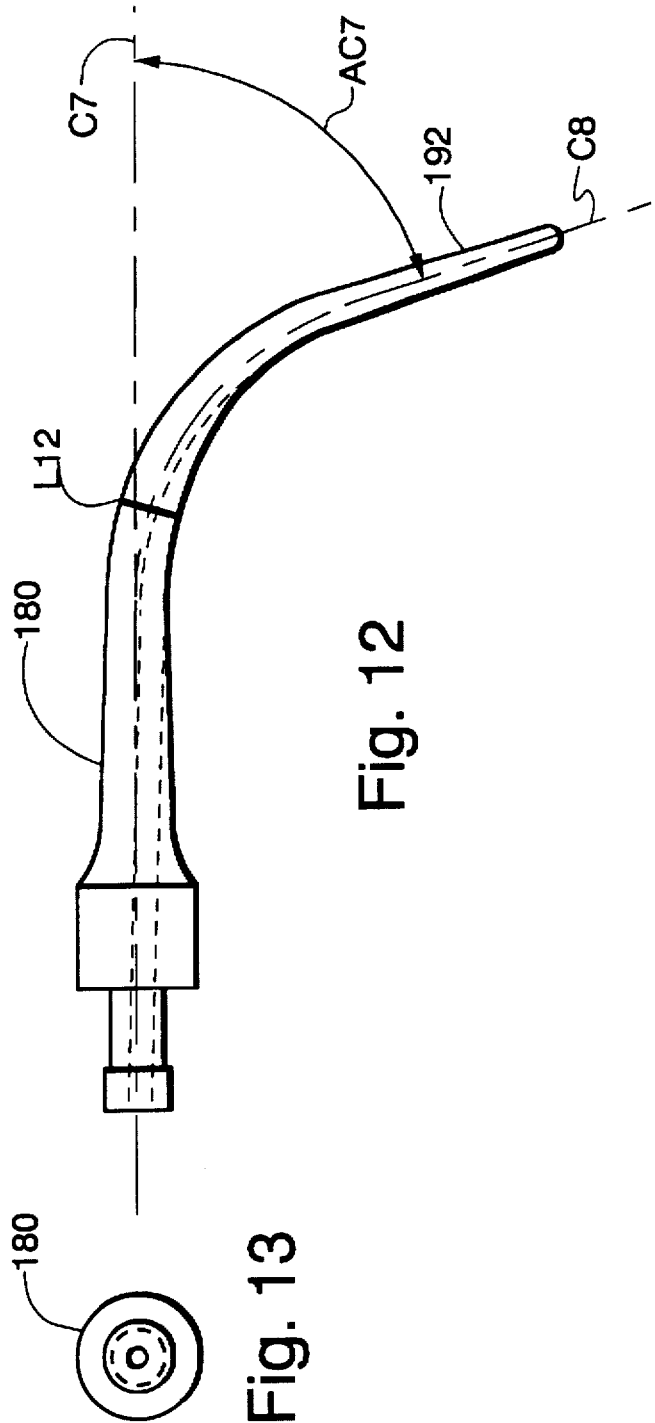

TRANSDUCER ACTIVATED SUBGINGIVAL TOOL TIP

This is a continuation-in-part of U.S. patent application Ser. No. 60/011072 (Case 1727-3CIP) filed Feb. 2, 1996 which is a continuation-in-part of U.S. patent application Ser. No. 60/010933 (Case 1727-2CIP) filed Jan. 31, 1996 which is a continuation-in-part of U.S. patent application Ser. No. PCT/US95/08363 filed Jun. 27, 1995 which is a continuation-in-part of U.S. patent application Ser. No. 08/268,418 filed Aug. 26, 1994 now U.S. Pat. No. 5,531,527.

BACKGROUND OF THE INVENTION

The invention relates to a transducer activated tool for contacting workpiece surfaces such as tooth surfaces and directing a fluid adjacent to the tooth. More particularly, the invention relates to an ultrasonically activated workpiece tool such as a subgingival dental instrument or insert therefore, including a vibrating tip for contacting tooth surfaces. The tip includes a conduit or passageway for directing a fluid onto the dental or tip surfaces. The end of the tip is adapted for subgingival insertion, and preferably the tip has an outer diameter of less than 0.03 inch within 0.03 inch of the end of the tip. During subgingival insertion the subgingival end of the tip extends between the patient's gum and the subgingival tooth surface, and delivers a focused spray of fluid onto the subgingival tooth surface.

Many useful dental instruments employ substantial vibratory motion at a tool tip of the instrument for cleaning, scaling and like operations. The tool tips are designed to produce flexural and longitudinal vibrations with flexural motions of from about 0.02 to 0.2 mm. The tip is typically attached to an electro-mechanical part or section that can be induced to vibrate at high frequency. The instrument is driven by an electronic generator at relatively high frequencies, typically on the order of above 20 kHz, to obtain adequate motion and to minimize objectionable noise since the human hearing threshold is about 18 kHz. The energy generator and related electro-mechanical section may be any one of several types such as electro-dynamic, piezo electric, or magnetostrictive. Design of the tip and its related electro-mechanical components involves combining a number of parameters to produce mechanical resonances (harmonic vibrations) at the driving frequency to produce amplified mechanical motion, particularly at the distal tip end.

Perdreaux in Re. 30,536 discloses an ultrasonic dental tool, wherein a handpiece containing a coil applies an electro-magnetic field to a magnetostrictive insert body to which a tool tip is fixed.

In a number of dental operations, the vibrating tip is guided over and about tooth surfaces by the operator. The tip must be capable of penetrating between teeth and under or below the gingival or gum line. Generally, the tip must be small in cross-section, ideally having a pointed tip with a tapered cross-section extending about 2.5 to 5 mm back from the distal tip end to allow adequate access between teeth and gingival (and to about 10 mm between teeth and subgingival)

Balamuth et al in U.S. Pat. No. 3,924,335 discloses a piezo electric crystal vibrated dental tool. Haydu in U.S. Pat. No. 3,488,851; Richman U.S. Pat. No. 3,589,012, Banko in U.S. Pat. No. 3,930,173, Robinson in U.S. Pat. No. 3,703,037 and Warrin in U.S. Pat. No. 5,125,837 discloses tips for dental apparatus.

The prior art does not provide a transducer activated subgingival tool for contacting subgingival tooth surfaces and directing a fluid adjacent to the surfaces, wherein the tool has an activated tip having a fluid inlet end, a subgingival outlet end, a step in the surface of the outer wall of the tip between said inlet end and the subgingival outlet end, and a fluid passageway wall internal to the tip.

SUMMARY OF THE INVENTION

The invention provides a transducer activated subgingival tool for contacting subgingival tooth surfaces and directing a fluid adjacent to the surfaces, wherein the tool has an activated tip having a fluid inlet end, a subgingival outlet end, a step in the surface of the outer wall of said tip between the inlet end and said subgingival outlet end, and a fluid passageway wall internal to the tip. The passageway wall is formed in the inlet end generally along the longitudinal center axis of the inlet end of the tip. The subgingival outlet end is shaped to contact the tooth surfaces. The fluid passageway has a central axis which is offset from the center axis of the inlet end of the tip such that the fluid passageway wall ends at an edge providing a fluid discharge orifice formed in the side of the tip and displaced from the center axis of the tip. The subgingival end of the tip has an outer diameter less than 0.03 inch within 0.03 inch from the terminus of the subgingival outlet end.

An activating transducer connecting body connects said tip to an activating transducer. A fluid source is connected to the passageway and provides a flow of fluid discharging from the passageway orifice.

In a preferred embodiment of the invention, the step intersects the passageway wall at the orifice edge. Preferably a line on, parallel to and extending from the outer surface of the outer wall of the inlet end of the tip adjacent to the step intersects the center axis of the tip forming a first angle with the center axis. A line on, parallel to and extending from the outer surface of the outer wall of the subgingival output end of the tip adjacent to the step intersects the center axis of the tip forming a second angle with the center axis. The first angle is greater than the second angle.

In a preferred embodiment of the invention, a first line on, parallel to and extending from the outer surface of the outer wall of the inlet end of the tip adjacent to and within 3 mm of the step intersects the center axis of the tip forming a first angle with the center axis. A second line on, parallel to and extending from the outer surface of the outer wall of the subgingival end of the tip adjacent to and within 3 mm of the step intersects the center axis of the tip forming the same angle as the first angle with the center axis. Preferably the first and second lines are at least 0.1 mm apart at the step.

Preferably the terminus of the outlet end of the tip has a centerline at the central axis of the tip at the terminus and the step has a centerline at the central axis of the tip. Preferably the tip is formed by bending the outlet end and the terminus centerline intersects the step centerline at an angle of at least 10 degrees. In another preferred embodiment of the invention, the tip is formed by bending the outlet end, and the terminus centerline does not intersect the step centerline.

In a preferred embodiment of the invention, the terminus centerline is laterally offset from the step centerline by at least 1 mm.

In a preferred embodiment, the tip fluid passageway is angularly offset from the tip longitudinal center axis such that the fluid discharge orifice is formed in a lateral surface of the tip such that the orifice center axis is located about 0.01 to about 8 mm from the distal end of said tip. In a most preferred embodiment, wherein the tip is a component of a dental tool, the fluid discharge orifice is located about 2-14 mm from the distal end of the tip. The tip includes a curved shape that depends upon its use and, most preferably, is of a universal shape useful in dental operations, having a distal portion bending from its centerline axis through an arc of about 60-90 degrees. The tool may be activated by sonic, ultrasonic, fluid or air means. The fluid delivered may be any fluid useful for the particular end use in which the tool is employed and is typically a saline solution, water or a solution comprising a medicament. The tool is particularly useful in dental, medical and veterinary uses. A preferred use of the tool is in dental operations such as cleaning, scaling, etc. A preferred tool tip is a component of an insert that is activated by an ultrasonic energy generator means. A preferred ultrasonically activated tool insert comprises a magnetostrictive element; a connecting body axially connected to the magnetostrictive element; and a tip, axially attached to the connecting body, the tip having distal surfaces shaped to contact a tooth, typically dental surfaces. In combination, the tip includes a fluid passageway internal to the tip, generally along the center axis of the tip, but offset from the axis such that a discharge orifice formed in said tip is displaced from the distal tip end center axis. In a preferred insert, the passageway is angularly offset from the tip axis by less than about 2 degrees such that the orifice exits within the range of 2-14 mm from the distal end of the tip. The insert is particularly useful for cleaning or scaling of teeth, and other dental procedures and, in such service, the distal end is typically bent through an arc of about 60-90 degrees.

The invention includes a method of making the tip, comprising machining step and taper angle of 2°-3° and 4°-10° and 3° and 4° at a transition of 8-14 mm from tip end and boring a passageway into a cylindrical rod, beginning at the center axis of an end of the rod and continuing at an angle of less than about 3 degrees from the center axis of said rod such that the passageway forms a discharge orifice 2-14 mm from the opposite distal end of the rod. A preferred method of forming the liquid passageway and discharge orifice is by means of electrical discharge machining. The bored cylindrical rod is then formed into a desired tip shape for contacting the desired tooth surfaces such as, for example, tooth surfaces. The cylindrical rod with two different angles may, optionally, be formed into a tapered tip at a transition about 8-14 mm from tip end or profile before being pierced, machined, bored or drilled for its internal fluid passageway.

The tip fluid passageway orifice may be offset eccentric to the tip axis, wherein the passageway is bored substantially parallel to the center axis of the tip but displaced from the axis by 0.1 to 0.5 mm.

BRIEF DESCRIPTION OF THE DRAWINGS

FIG. 1 is a sectional view of an ultrasonically activated tool tip of the invention as a component of a dental tool insert in combination with a handpiece.

FIG. 4 is a side view of a subgingival tip in accordance with a preferred embodiment of the invention.

FIG. 5 is a bottom view of the tip shown in FIG. 4.

FIG. 6 is a end view of the tip shown in FIG. 4.

FIG. 7 is a side view of a subgingival tip in accordance with a preferred embodiment of the invention.

FIG. 7A is a partial cross-sectional side view of the tip shown in FIG. 7.

FIG. 8 is a bottom view of the tip shown in FIG. 7.

FIG. 9 is a end view of the tip shown in FIG. 7.

FIG. 10 is a side view of a subgingival tip in accordance with a preferred embodiment of the invention.

FIG. 11 is a end view of the tip shown in FIG. 10.

FIG. 12 is a side view of a subgingival tip in accordance with a preferred embodiment of the invention.

FIG. 13 is a end view of the tip shown in FIG. 12.

DETAILED DESCRIPTION OF PREFERRED EMBODIMENTS

The invention is now described with more particular reference to FIGS. 1-18. In general, a transducer activated tool for contacting tooth surfaces and directing a fluid onto the tooth. A principal element of the invention is an activated tip comprising distal surfaces that are shaped to contact the tooth surfaces. Additionally, the tip includes a fluid passageway internal to the tip extending substantially along the longitudinal center axis of the tip but offset such that a fluid discharge orifice is formed displaced from the distal tip axis. A connecting body connects the tip to an activating transducer and a fluid source is connected to the tool to supply a flow of fluid through the fluid passageway such that it discharges from the passageway orifice.

A key advantage of the activated tip of the invention is that the fluid passageway and its discharge orifice arrangement relate to the distal end of the tip such that the arrangement does not weaken the tip distal portion by removing metal or materials of construction at a critical portion of the tip at its points of maximum stress. Secondly, the fluid discharge orifice of the arrangement of the invention is located at or near a node of flexural motion and not near a flexural loop such that spray or mist generation at the orifice is minimized.

Figure 2:
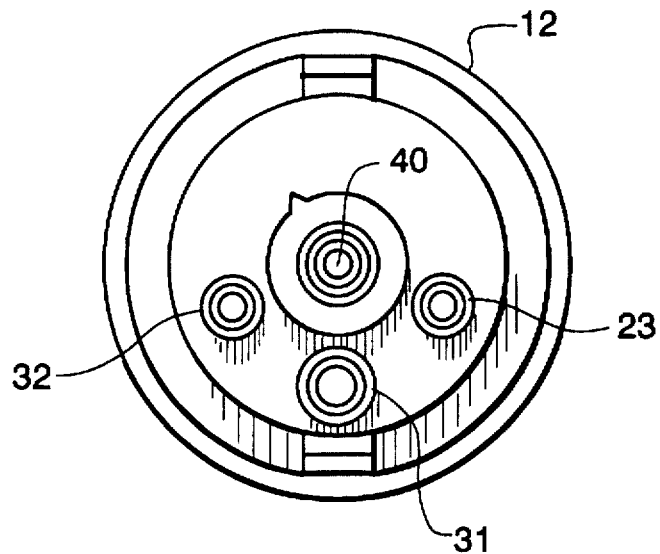
FIG. 2 is an end view of the handpiece component with the electrical/fluid supply connectors detached.
Figure 3:
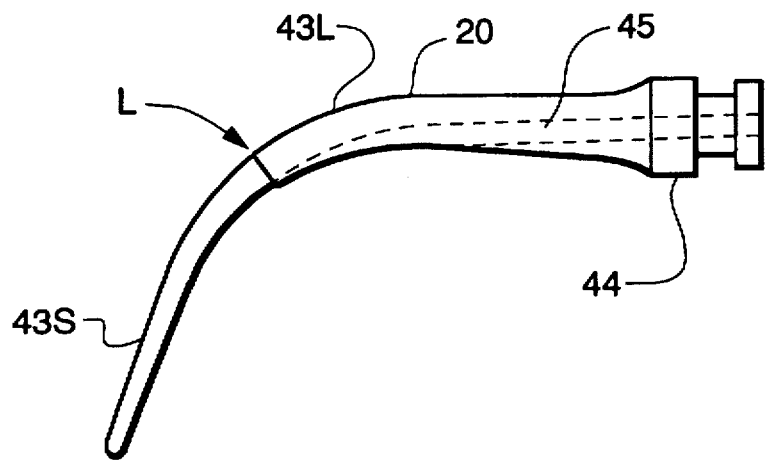
FIG. 3 is an enlarged sectional view of a tip of the invention having an angularly offset fluid passageway.

Referring to the drawings, FIGS. 1 and 2 show a preferred embodiment of the invention wherein the tip is a component of an ultrasonically activated tool 10 for dental use, comprising a dental tool insert 11 in combination with a handpiece 12.

The general configuration of the tool of the invention is well known in the art and is similar to the ultrasonic device described by Perdreaux in Re. 30,536. The tool insert 11 includes a tool tip 20, a key element of the invention which will be described in more detail below, and a magnetostrictive element 14, joined by a connecting body 15. A portion of the connecting body 15 is enclosed in a sleeve 16 which is formed to enclose a portion of the connecting body 15 such that the connecting body is free to transmit energy to the tip. In addition, the sleeve forms an annular passageway 17 permitting fluid flow to the tip 20. A reduced end cross-section of the sleeve 16 permits it to be removably inserted into the housing 12. An O-ring 18 fits into a groove cut into the sleeve providing a retaining, frictional fit therebetween. The internal posterior face 19 of this section is countersunk to facilitate fluid flow about the connecting body. At the distal end of the sleeve, its internal bore is fitted with a groove and O-ring 21 which, in combination with the connecting body 15, provide a seal for preventing fluid from flowing from the assembled sleeve and connecting body.

The connecting body 15 functions as an acoustical impedance transformer for transporting energy from the magnetostrictive stack 14 to the work tool tip 20. As is well known in the art, the connecting body 15 varies in cross-section along its longitudinal length which varies the amplitude of mechanical vibration, with the ultimate object of obtaining a desired amplitude magnification at the operating tip that is useful for performing a task on a tooth. These principals are well described by Banko in U.S. Pat. No. 3,930,173, which is incorporated herein by reference. As described by Banko, the cross-section and, hence, mass, of the various portions of the connecting body are designed to appropriately locate nodes and loops of longitudinal vibration. As noted therein a nodal point is where the amplitude of longitudinal vibration is zero and internal stress in the connecting body is greatest while a loop is a point where longitudinal motion is at its greatest and stress the least. Thus, it is desirable to locate supporting and sealing O-rings and the like at nodal points.

The connecting body 15 includes a ring 22 brazed or machined onto its shaft adjacent to the nodal point and sized to fit loosely into a corresponding groove 23 cut into the sleeve interior surface. The ring 22 includes a single key (not shown) on its outer circumference that fits into one of two semicircular bypasses (not shown) cut longitudinally into the interior surfaces of the bore, 180° apart from each other and centered with a radius or altitude of the groove 23. The key is held in one of the bypasses after assembly which serves as a retainer for the key while the other bypass provides a path for fluid flow around the ring.

Brazed or otherwise firmly attached to the connecting body 15 is the magnetostrictive vibrator or stack 14 which is preferably formed of a metal alloy such as permanickel, nickel or other alloys that possess high tensile strength and are highly magnetostrictive in character.

The housing or handpiece 12 includes a coil unit 24 that produces a magnetic field for inducing motion longitudinally to the insert 11 through the magnetostrictive stack 14. The coil unit includes a drive coil 25 that is connected to an alternating current source. The drive coil 25 is wound in a double coil between retaining flanges 26, 27 and provides an electromagnetic field in the handpiece 12. A feedback coil 28 of fine wire is provided to register voltage developed by the insert in the electromagnetic field and the handpiece. The feedback coil is a winding of five layers of wire, between flanges 29, 30, and is connected to ground terminal 31 and terminal 32, shown in FIG. 2. A bucking coil 34, of heavier wire than the feedback coil is wound in one layer over the feedback coil and is designed to minimize transformer coupling between the drive coil and the feedback coil. The bucking coil and drive coil are connected between terminals 31 and 33 in one continuous wire. The drive coil is attached to terminal 33 and, using a right hand turn for example, is wound from flange 26 to flange 27 and back. The end of the wire is then connected to terminal 31. The bucking coil and drive coil are wired in series and are wound in opposite direction and are therefore electromagnetically 180 degrees out of phase. The bucking coil is electrically insulated from the feedback coil.

Electrical power and fluid are supplied to the instrument by means of a cable 35, including a plug attachment 36 that connects to the handpiece. The electrical supply is connected through three electrical pin connectors 37 (only one shown) that mate with the handpiece receptacle terminals shown in FIG. 2. Pin connectors connected to the terminals 32, 33 provide power to the coil and register feedback while a pin connected to a grounded terminal 31 acts as a common ground. The cable 35 also includes a fluid conduit 38 and a connector fitting 39 for attachment to the body of the handpiece. The conduit supplies fluid to the handpiece, and, ultimately, the tool tip 20, through a passageway 40, initially into contact with the magnetostrictive element 14 to provide cooling.

At the distal end of the connecting body 15, the connecting body is counter-bored to form a central axial longitudinal passageway 41 for fluid flow to the tip 20. A radial boring 42 in the connecting body 15 at the interior terminus of the fluid passageway boring connects the central passageway 41 with the interior of the sleeve 16 to collect fluid flowing from (shown in the drawings as small arrows) about the magnetostrictive element. The radial boring 42 is located on the internal side of the O-ring gasket 21 so that flow of fluid from the handpiece interior is only from the central bore 41 out of the connecting body.

The tip 20, the operative portion of the ultrasonically activated tool, comprises a smaller diameter distal tip portion 43S for contacting tooth surfaces, larger diameter portion 43L and a shank portion 44 that is secured to the connecting body 15. Smaller diameter portion 43S intersects larger diameter portion 43L at a tip surface angle transition line L. The connecting body includes a counter bore for receiving the tip shank 44 which may be secured by brazing, mating threads or the like. A fluid passageway 45, described in detail below, formed interior to the tip element or body, exits through a internal or side wall in the tip to provide a fluid discharge orifice 46.

Referring to FIG. 1, in operation, an alternating current impressed upon the coil unit 24 described above creates an alternating magnetic field in the handpiece portion 12 surrounding the magnetostrictive stack 14. The electromagnetic field vibrationally excites the magnetostrictive stack 14, imparting longitudinal motion at ultrasonic frequency to the connecting body 15 and tip 20 connected thereto. As discussed above, the longitudinal motion causes the distal end 43 of the tip 20 to vibrate flexurally to produce a motion useful for performing a task on a tooth, such as, for example, cleaning a tooth. Simultaneously, a flow of cooling/irrigating fluid flows into the handpiece chamber containing the magnetostrictive stack, cooling the stack and passing therefrom into the annular space between the sleeve 16 and connecting body 15. The fluid leaves the connecting body discharge passageway and flows into the tip passageway 45, discharging from the discharge orifice 46 onto the tooth surfaces, providing cooling and cleaning or other desired effects depending upon the character of the fluid applied and tooth operated on. The tips shown in FIGS. 4–17 are adapted to be used in place of tip 20 in handpiece 12.

With more particular reference to FIGS. 4–6 subgingival tip 120 is seen. Tip 120 has flange 122 joined by connecting member 124 to flange 126. Tip 120 has upper body end 128 joined along shoulder (or step) 130 to lower body end 132. Shoulder 130 has curved side wall 131. Tip central axis C1 intersects passageway central axis C2 at angle AC1. A line extending from and parallel to side A2 or A2' intersects central axis C1 at an angle which is larger than the angle of intersection with central axis C1 by a line extending from and parallel to side A1 or A1'.

A straight line UL5 is on, parallel to and extending from the outer surface of the outer wall 121 of the upper body inlet end 128 of tip adjacent to and within 3 mm of shoulder (or step) 130. Line UL5 forms a first angle ASC2–ASC2' with the centerline of center axis C1. A line LL5 is on, parallel and extending from the outer surface 123 of the outer wall of the lower body subgingival end of tip 120 adjacent to and within 3 mm of the step 130. Line LL5 forms an angle ASC1–ASC1' with the centerline of center axis C1, and lines UL5 and LL5 are at least 0.1 mm apart at the step 130. Angle ASC2–ASC2' is preferably within 0.5 degrees of angle ASC1–ASC1', more preferably within 0.2 degrees and most preferably within 0.05 degrees. Preferably the step intersects the passageway wall edge 134 which forms an orifice.

With more particular reference to FIGS. 7–9 subgingival tip 140 is seen. Tip 140 has flange 142 joined by connecting member 144 to flange 146. Tip central axis C3 intersects passageway central axis C4 at angle AC3.

A straight line UL7A on the outer surface of the outer wall of the upper body 140U of the inlet end of tip 140 adjacent to the step L8 forms a first angle A8–A8' with the center axis C3. A line LL7A on the outer surface of the outer wall of the lower body 140L of the subgingival end of the tip of tip 140 adjacent to step L8 forms a second angle A9–A9' with the center axis C3. Angle A8–A8' is greater than angle A9–A9'. The difference between angle A8–A8' and angle A9–A9' is preferably less than 2 degrees, more preferably less than 1 degree and most preferably about 0.5 degree. Preferably the angle of intersection between the lines UL7A and LL7A is less than 2 degrees and more preferably about 1 degree. Preferably step L8 circumscribes tip 140 from the passageway wall edge 154 at one side of the orifice to passageway wall edge 155 at the opposite side of the orifice. Preferably step L8 is less than 3 mm wide, more preferably less than 1 mm wide and most preferably less than 0.5 mm wide. Preferably the step L8 is in a plane which extends along center axis C3 a distance of less than 3 mm, more preferably less than 1 mm. Preferably the lines UL7A and LL7A are each straight and extend at least 1 mm in length in opposite directions from step L8 while in continuous contact with an adjacent outer surface of tip 140.

Preferably the lower portion of tip 140 between step L8 and terminus T7 is from 8 to 14 mm in length. Thus, the distance from the terminus T7 of tip 140 to step L8 is preferably from 8 to 14 mm in length. Most preferably the distance from the terminus T7 of tip 140 to the step L8 is from 9 to 11 mm in length.

With more particular reference to FIGS. 10 and 11 subgingival tip 160 is seen. Tip 160 has step 170, flange 162 joined by connecting member 164 to flange 166. Step 170 has curved side 171. Tip central axis C5 intersects passageway central axis C6 at angle AC5.

With more particular reference to FIGS. 12 and 13 subgingival tip 180 is seen. Tip 180 has step L12, flange 182 joined by connecting member 184 to flange 186. Tip central axis C7 intersects passageway central axis C8 at angle AC7. Tip 180 is preferably made by bending a straight tip having a passage therein such as tip 140 shown in FIGS. 7–9.

Figure 14:
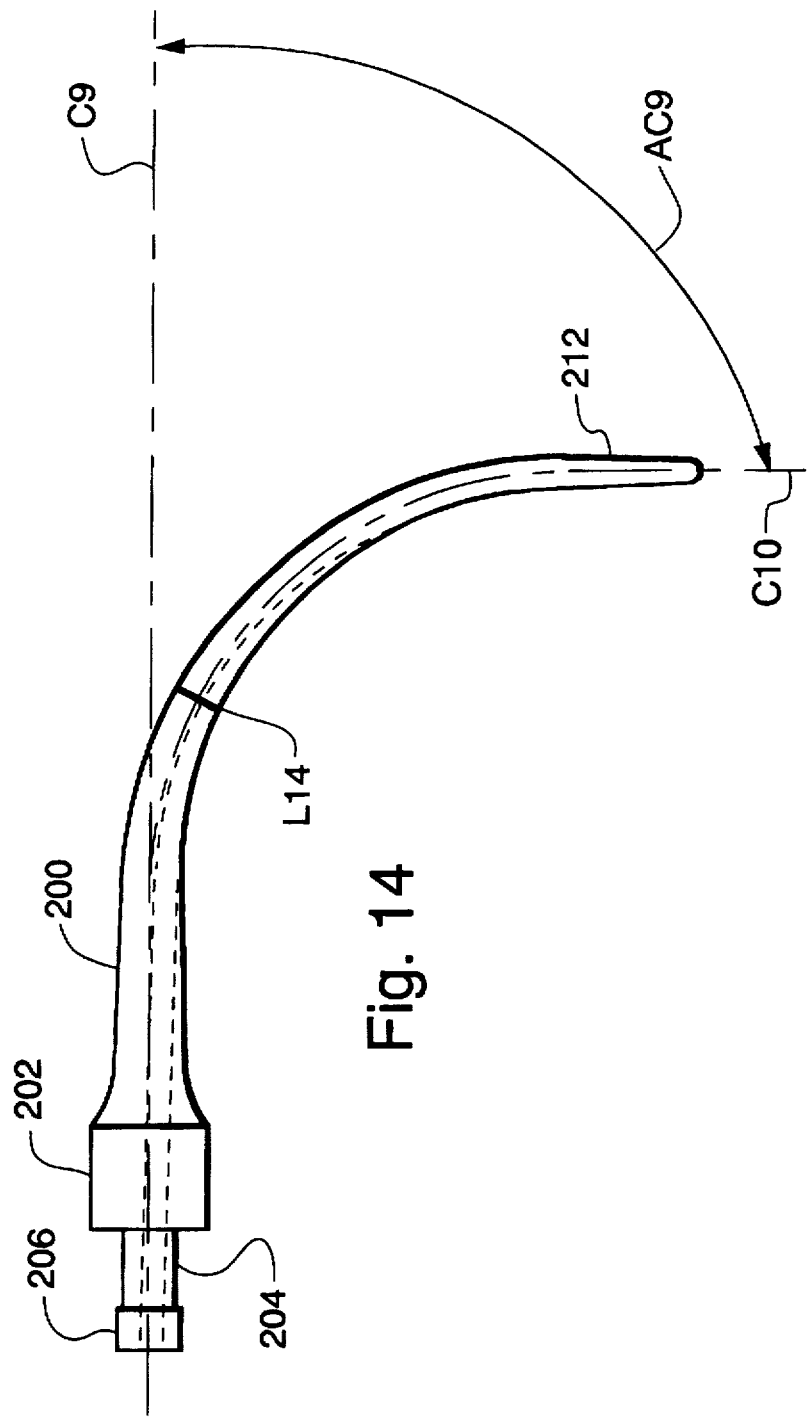
FIG. 14 is a side view of a subgingival tip in accordance with a preferred embodiment of the invention.

With more particular reference to FIG. 14 subgingival tip 200 is seen. Tip 200 has step L14, flange 202 joined by connecting member 204 to flange 206. Tip central axis C9 intersects central axis C10 of an internal passageway at angle AC9. Tip 200 is preferably made by bending a straight tip having a passage therein such as tip 140 shown in FIGS. 7–9.

Figure 15:
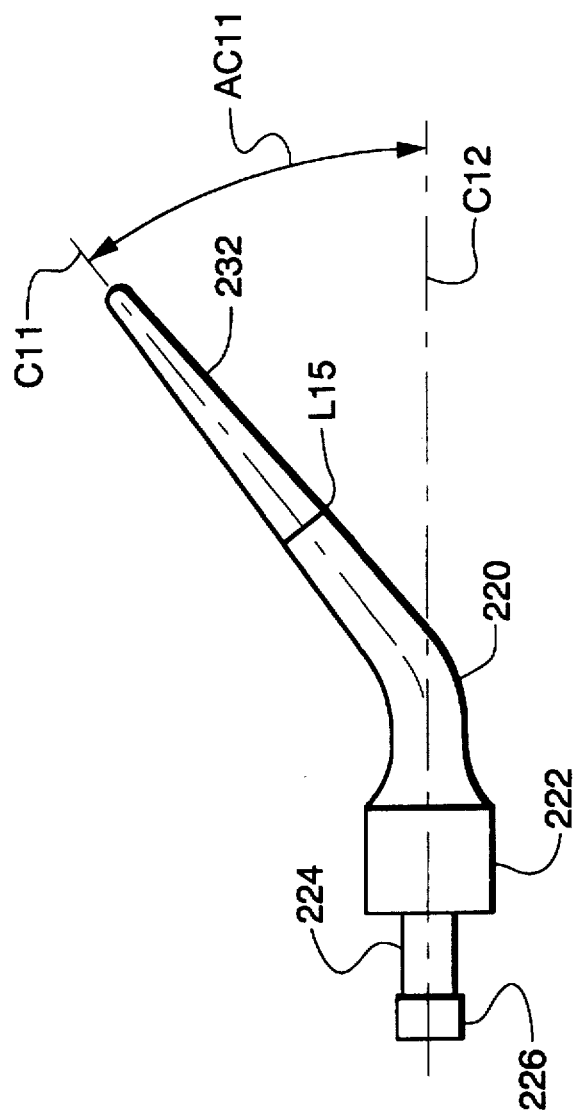
FIG. 15 is a side view of a subgingival tip in accordance with a preferred embodiment of the invention.
Figure 15A:
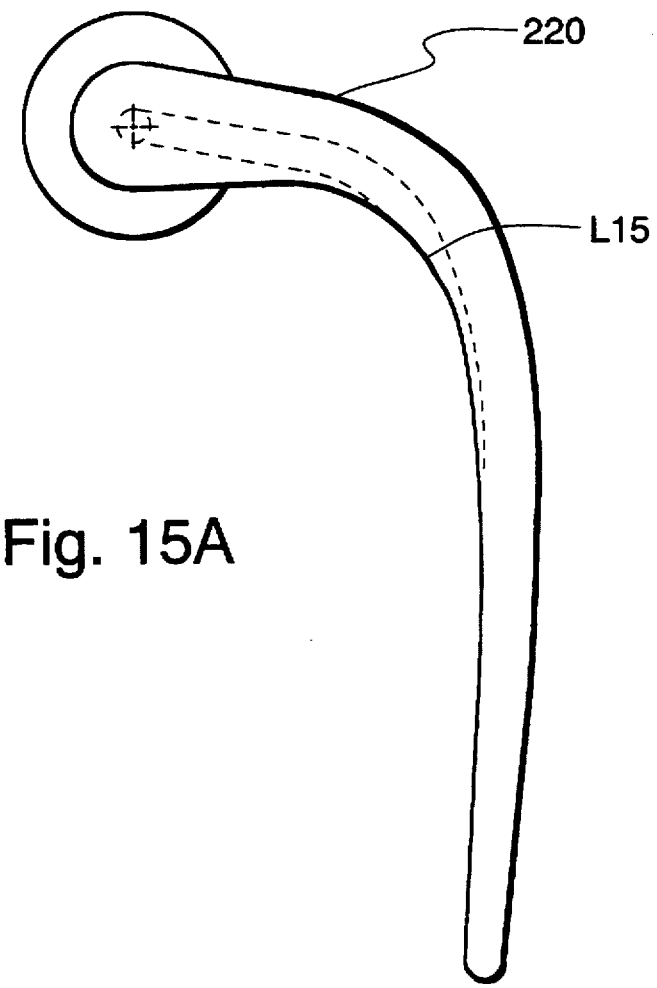
FIG. 15A is an end view of the subgingival tip shown in FIG. 15.

With more particular reference to FIGS. 15 and 15A subgingival tip 220 is seen. Tip 220 has step L15, flange 222 joined by connecting member 224 to flange 226. Tip central axis C11 intersects central axis C12 of an internal passageway at angle ACC11. Tip 220 is preferably made by bending a straight tip having a passage therein such a tip 140 shown in FIGS. 7–9.

Figure 16:
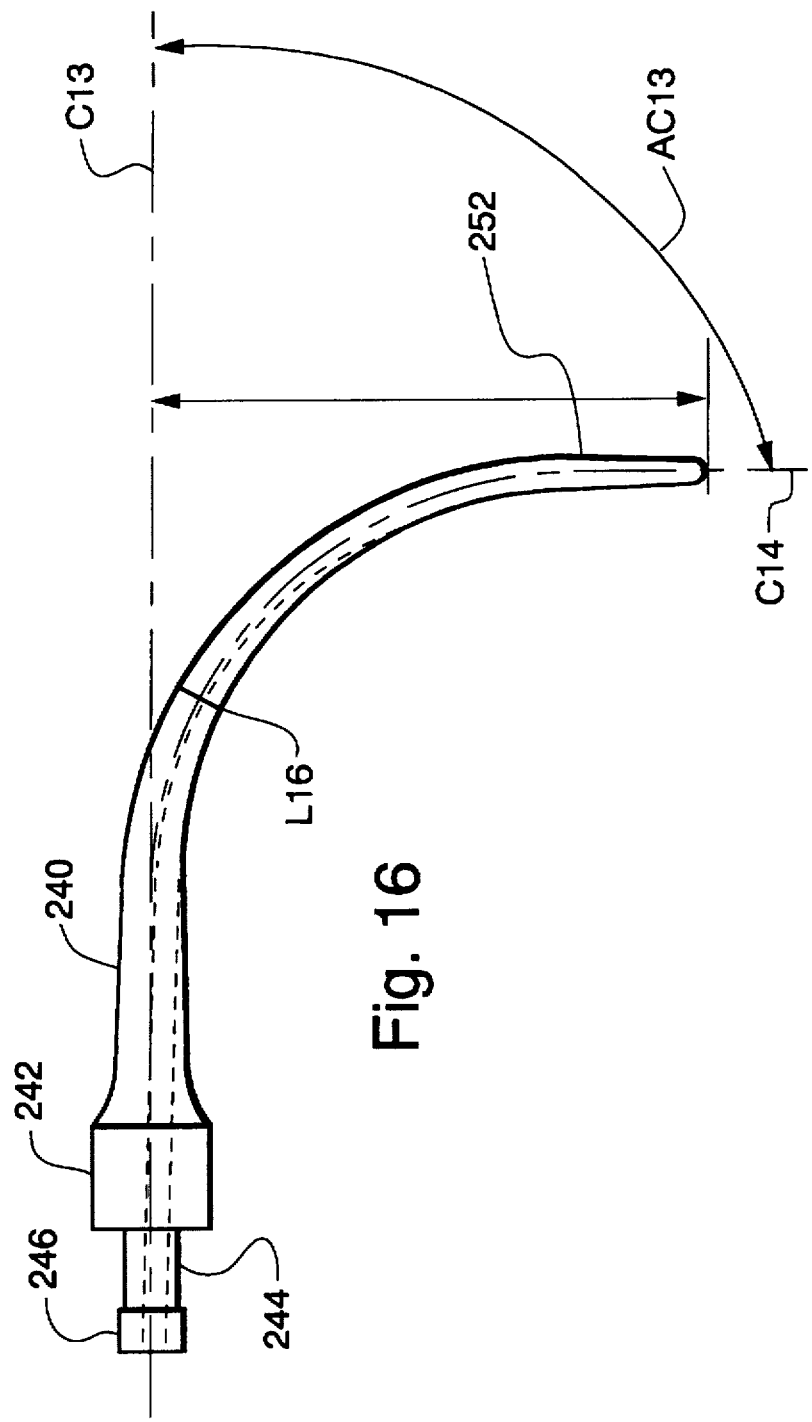
FIG. 16 is a side view of a subgingival tip in accordance with a preferred embodiment of the invention.

With more particular reference to FIG. 16 subgingival tip 240 is seen. Tip 240 has step L16, flange 242 joined by connecting member 244 to flange 246. Tip central axis C13 intersects central axis C14 of an internal passageway at angle AC13. Tip 240 is preferably made by bending a straight tip having a passage therein such a tip 140 shown in FIGS. 7–9.

Figure 17:
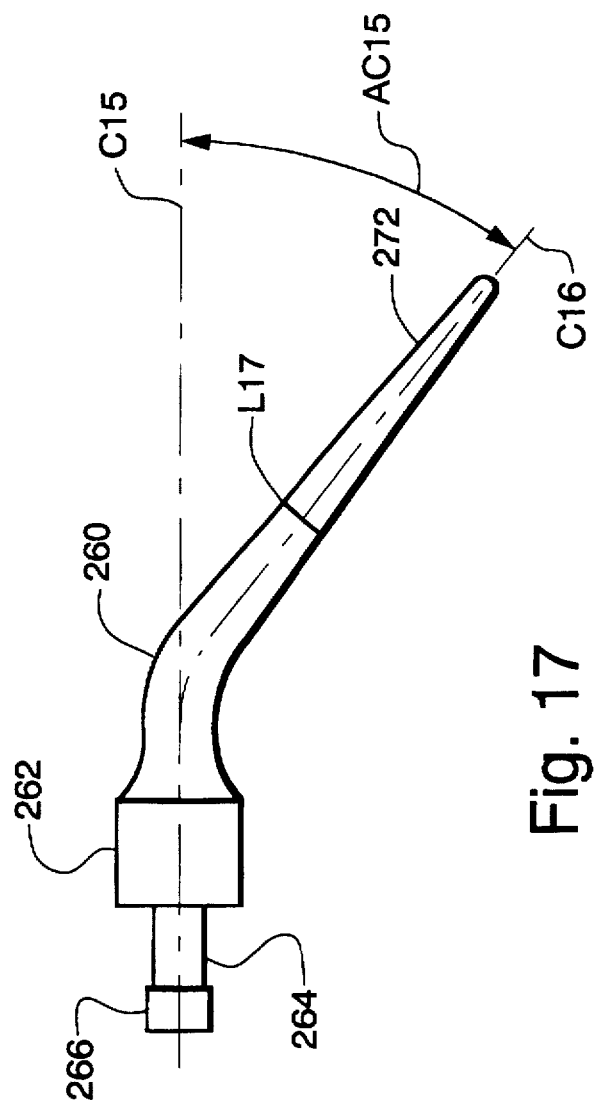
FIG. 17 is a side view of a subgingival tip in accordance with a preferred embodiment of the invention.
Figure 18:
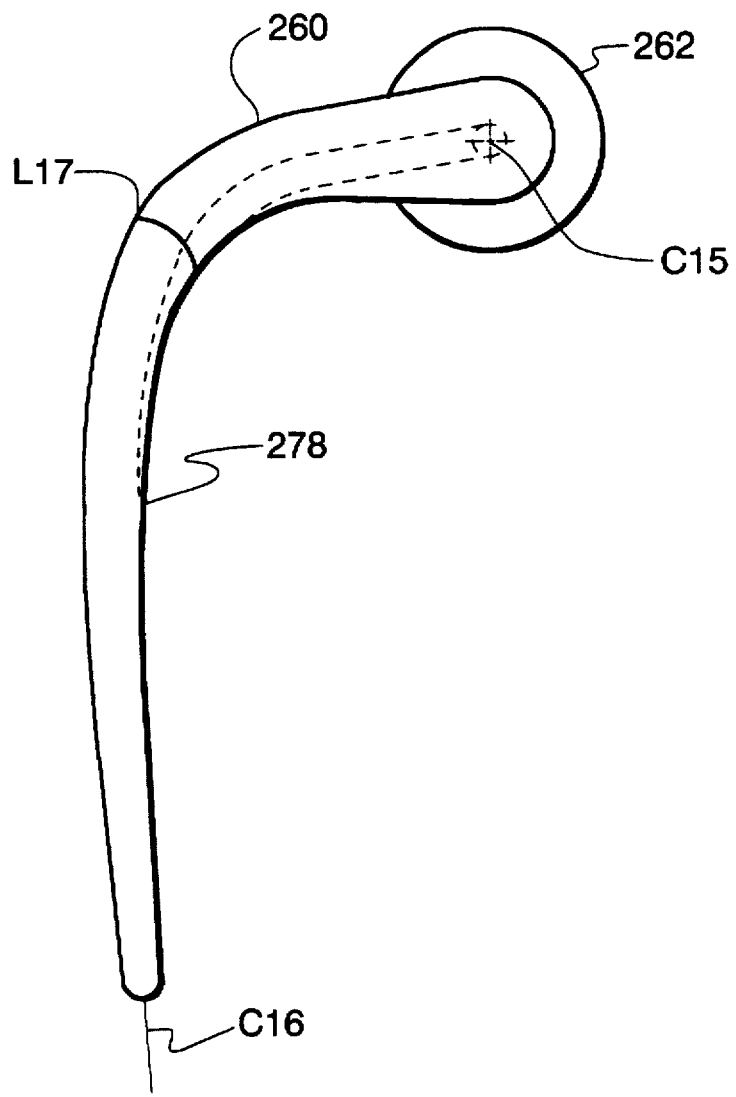
FIG. 18 is an end view of the tip shown in FIG. 17.

With more particular reference to FIGS. 17 and 18 subgingival tip 260 is seen. Tip 260 has step L17, flange 262 joined by connecting member 264 to flange 266. Tip central axis C15 intersects central axis C16 of an internal passageway at angle AC15. Step L17 intersects passageway wall 278 at an edge which forms an orifice. Tip 260 is preferably made by bending a straight tip having a passage therein such a tip 140 shown in FIGS. 7–9.

It is clear from the invention that the nature of the device activating the tool longitudinally is not a limitation. The tool may be electronically activated by means of electromagnetostrictive elements as discussed or piezo electric crystals or other means, including air or water activation. While the preferred embodiment of the invention focuses upon use of the tool for dental operations, such as cleaning and scaling, it is intended that the instrument have broad use and application wherever it is desirable to act on a tooth surface with a vibratory motion with simultaneously providing fluid to irrigate the tip and tooth surfaces. The exact dimensions of the tip are determined by the operation for which the tip is employed. A typical tip shank diameter is 0.065 inches (1.65 mm) for certain dental application, such that the tip end can be tapered to a diameter small enough to fit into narrow crevices and areas between teeth. The exact location of the discharge orifice of the fluid is determined by many factors, including the frequency of operation as well as the transducer employed.

The nature of the fluid delivered to the tooth is dependent upon the operation to be performed on or at the tooth. In a dental cleaning environment, water is a useful fluid for cooling and removal of debris. In other uses it may be preferred to employ a saline solution, sterile water or a solution containing some selected medicament to achieve a particular purpose.

The nature of the passageway drilled within the tip is not critical. Conventionally, it will be a straight, linear bore. However, it is within the scope of the invention if a bore is curved. The essence of the invention is to establish a discharge orifice that maximizes the amount of material or metal remaining at or on the tip end for flexural strength while providing an orifice location with respect to the tip motion where spray is minimized.

The tip may be formed of any material that has sufficient strength under the longitudinal and flexural stresses to which it is subjected. Typically, a high strength stainless steel is utilized but the tip may be formed of engineered polymerics or other materials, such as carbon-filled polycarbonate, graphite composites or other materials that have sufficient hardness and elasticity to accommodate the motional stresses and wear of the operation.

It is noted that the tool tip of the invention is depicted in cross-section as cylindrical, tapering to a relatively small diameter and reduce to another taper angle to use in subgingival area. It is well known in the art that tools may have other configurations and cross-sections and such tools are within the scope of the invention. Whether the resulting tool tip is rectangular, irregular shaped or some other shape in cross-section or includes some configuration other than a tapered point at the working tip, it is preferred that the discharge exit be located from the terminal end of the tip at or just before the flexural node where there is the lowest flexural motion and the orifice exit is least likely to cause fracture stresses in the tip. The invention must also be located distant from harmonic loops where motion is greatest which tend to create excessive sprays. Such a loop is typically 7-9 mm from the tip end, for this preferred embodiment of this invention.

The particular characteristics of the shape of the tip, that is, bending radii, length of bent arc, length of section beyond the bend, tip tapers and the material from which the tip is fashioned, all contribute to the performance characteristics of the tip in flexure. The design of the tip, generally, and of the FIG. 4 tip in particular, utilizes the factors described above to provide a gain or amplification of the longitudinal vibrational motion produced by the insert, of from two to five fold.

The tip of the invention may be produced by a number of milling techniques. A preferred method first requires that the tip body is formed of cylindrical rod drawn to a diameter that is slightly larger than the finished tip diameter. The selected material is one that is corrosion resistant, of high tensile strength, high sheer strength, high fatigue limit, good toughness and that can be bent machined and/or formed. The rod is milled to substantially its final configuration before shaping and bending. The fluid passageway is formed in the tip body by means of a number of techniques including drilling and boring. Typically, after forming the passageway, the tip is machined, formed or bent to its useful finished shape and configuration.

A preferred boring method is by means of electric discharge machining (EDM), a process that insures that the passageway is angled to break out on a wall surface of the tip rod on the convex side of the existing or intended bend, preferably 5 to 14 mm from the end of the tip. In EDM, the passageway of a desired diameter is formed by a DC current that generates rapid repetitive spark discharges through a film of dielectric fluid flowing between the workpiece and a shaped electrode tool. An EDM system Model No. SP-1M, manufactured by Japan EDM Products, Division of Mitsui Machine Technology, Inc. of Glendale Heights, Ill., was employed to form 0.018 inch (0.45 mm) diameter fluid passageways for the tip of the invention.

Alternatively, the passageway is bored into the tip body or cylinder using a lathe that is equipped with a tail stock that can be offset. The offset is adjusted, for example, sufficient to produce an angle of 1 to 1.6 degrees from the centerline of the tip body cylinder. This is equivalent to an offset distance of 0.4 to 0.6 mm at the end of the cylinder. The passageway is drilled and the offset tailstock of the lathe is returned to its centering position, aligned with the live or driven center of the lathe. The blank is then machined, for example, to provide tapering, to its final design dimensions. The result will be a tip blank that has its internal fluid passageway centered at the large end of the blank and exiting at a cylindrical wall displaced from but near the small end of the tip. This process produces a blank that is of uniform cross-section taper at a larger angle typically 4°–6° and tapering again at smaller angle typically 2°–3° near the end of the tip, where vibrational stresses are greatest and maximum material within the design parameter is needed for strength. Maximum strength is achieved by this method because the machine tip blank has remained concentric to its maximum strength orientation formed along its longitudinal axis during drawing. The resulting tip will have a fluid outlet located 2 to 8 mm from the end of the tip.

Preferably the step circumscribes the tip from the passageway wall at one side of the orifice to the passageway wall at the other side of the orifice. Preferably the step is less than 3 mm wide, more preferably less than 1 mm wide and most preferably less than 0.5 mm wide. Preferably the lines are straight and at least from 1 mm in length.

Preferably the output portion of the tip is from 8 to 14 mm in length. That is the distance from the terminus of the tip to the step (the output portion) is preferably from 8 to 14 mm long. Most preferably the distance from the terminus of the tip to the step is from 9 to 11 mm in length.

It will be apparent to those skilled in the art that various modifications and changes may be made in the practice and use of the present invention without departing from the scope thereof as set forth in the following claims.

We claim:

1. A transducer activated subgingival tool for contacting subgingival tooth surfaces and directing a fluid adjacent to said surfaces, comprising:

an activated tip having a fluid inlet end, a subgingival outlet end, a step in the surface of the outer wall of said tip between said inlet end and said subgingival outlet end, and a fluid passageway having a wall internal to said tip formed in said inlet end generally along the longitudinal center axis of said inlet end of the tip, said subgingival outlet end being shaped to contact said tooth surfaces, said fluid passageway having a central axis which is offset from said center axis of said inlet end of the tip such that said fluid passageway wall ends at an edge providing a fluid discharge orifice formed in the side of said tip and said passageway being displaced from said center axis of said tip, the length of said subgingival end of said tip within 0.03 inch from the terminus of said subgingival outlet end, having an outer diameter less than 0.03 inch;

an activating transducer connecting body connecting said tip to an activating transducer; and a fluid source connected to said tip fluid passageway and providing a flow of fluid discharging from said tip fluid passageway discharge orifice.

2. The tool of claim 1 wherein said step intersects said passageway wall at said edge providing an orifice.

3. The tool of claim 1 wherein a straight line parallel to and extending from the outer surface of said outer wall of said inlet end of said tip adjacent to said step intersects with said center axis forming a first angle with said center axis, a straight line parallel to and extending from the outer surface of said outer wall of said subgingival end of said tip adjacent to said step intersects with said center axis forming a second angle with said center axis, and said first angle is greater than said second angle by at least 0.25 degree and less than 5 degrees.

4. The tool of claim 1 wherein a first line on, parallel to and extending from the outer surface of said outer wall of said inlet end of said tip adjacent to and within 3 mm of said step intersects with said center axis forming a first angle with said center axis, a second line on, parallel to and extending from the outer surface of said outer wall of said subgingival end of said tip adjacent to and within 3 mm of said step intersects with said center axis forming said first angle with said center axis, and said first and second lines are at least 0.1 mm apart at said step.

5. The tool of claim 1 wherein the terminus of said outlet end of said tip has a centerline at the central axis of said tip at said terminus, and said step has a centerline at the central axis of said tip.

6. The tool of claim 5 wherein said tip is formed by bending said outlet end and said terminus centerline intersects said step centerline at an angle of at least 10 degrees.

7. The tool of claim 5 wherein said tip is formed by bending said outlet end, and said terminus centerline does not intersect said step centerline.

8. The tool of claim 7 wherein said terminus centerline is laterally offset from said step centerline by at least 1 mm.

9. The tool of claim 1 wherein said tip fluid passageway is angularly offset from the tip longitudinal center axis such that said fluid discharge orifice is formed in a lateral surface of said tip.

10. The tool of claim 9 wherein said fluid passageway is angularly offset from the center axis of the tip by less than about 3 degrees.

11. The tool of claim 9 wherein said fluid passageway is angularly offset from the centerline of the tip by less than about 2 degrees and said passageway wall edge is about 2–14 mm from the terminus of said outlet end of said tip.

12. The tool of claim 1 wherein said fluid discharge orifice has an orifice center line and the center point on said orifice center line is about 0.01 to about 8 mm from the distal end of said tip.

13. The tool of claim 1 wherein said activating transducer activates said tip by sonic, ultrasonic, fluid or air means and said activating transducer is a piezo crystal.

14. The tool of claim 1 wherein said discharge fluid is saline, water or a solution comprising a medicament.

15. The tool of claim 1 wherein said tip is connected to said connecting body by threads, press fit, soldering, brazing or welding.

16. The tool of claim 15 wherein said tip shape comprises at least two bends.

17. The tool of claim 16, said tip fluid discharge orifice located on a concave surface within about 10 mm from the outlet end.

18. The tool of claim 1 wherein said tip is formed of stainless steel, alloys, carbon filled polycarbonate or graphite composite material.

19. The tool of claim 1 wherein said tip has a bend from its centerline axis through an arc of from about 60 to about 90 degrees.

20. The tool of claim 1 wherein said tip fluid passageway orifice is eccentrically offset from said tip axis, wherein the passageway is substantially parallel to the center axis of the tip but displaced from said axis by 0.1 to 0.5 mm.

21. The tool of claim 20 wherein said tip distal end is shaped to contact subgingival tooth surfaces and said fluid discharge orifice is located such that said fluid impinges upon said tooth surfaces.

22. An insert for an ultrasonically activated subgingival tool of a generally axially elongated cylindrical structure comprising a handpiece including a coil for generating an electromagnetic field, said insert being vibrated at high frequency in longitudinal motion in response to said coil, said insert comprising:

a magnetostrictive element;

a connecting body, axially transmitting said high frequency motion from said ultrasonic magnetostrictive element; and a tip, axially attached to said connecting body, that receives said longitudinal motion, having distal surfaces shaped to contact a subgingival tooth surface, said tip comprising, a fluid passageway having a wall extending internally through a substantial portion of said tip, formed generally along the longitudinal center axis of said tip, said tip having an inlet end and a subgingival outlet end, said subgingival outlet end extending to a tip terminus, said inlet end and said subgingival outlet end extending in opposite directions from a step, said step being a topographical change in the outer surface of the tip, said input end and said output end each having one or more cross sectional dimensions, the longest cross-sectional dimension of said output end being smaller than the smallest cross-sectional dimension of said input end, said subgingival end being shaped to contact said subgingival tooth surfaces without damaging the adjacent gum, a 0.03 inch length of said subgingival end of said tip within 0.03 inch of said tip terminus having one or more outer diameters, each of said diameters being less than 0.03 inch.

23. The insert of claim 22 wherein said step intersects an orifice in said passageway wall.

24. The insert of claim 22 wherein a line on the outer surface of an outer wall of said tip of said inlet end adjacent to said step forms a first angle with said center axis, a line on the outer surface of said outer wall of said tip of said subgingival outlet end adjacent to said step forms a second angle with said center axis, and said first angle in greater than said second angle.

25. The insert of claim 22 wherein a line on the outer surface of said outer wall of said tip of said inlet end adjacent to and within 3 mm of said step forms a first angle with said center axis, a line on the outer surface of said outer wall of said tip of said subgingival end adjacent to and within 3 mm of said step forms said first angle with said center axis, and said lines are at least 0.1 mm apart at said step.

26. The insert of claim 22 wherein said passageway is angularly offset from said tip axis by less than about 3 degrees.

27. The insert of claim 26 wherein said tip passageway orifice exits within a range of about 2–14 mm from the distal end of said tip.

28. The insert of claim 22 wherein said tip comprises a shoulder of 10 mm or less in length.

29. The insert of claim 28 wherein said passageway wall is offset from said axis such that a discharge orifice formed in said tip is displaced from a distal tip end center axis.

30. The insert of claim 22 wherein said fluid passageway is eccentrically offset from said tip axis, wherein said passageway is formed substantially parallel to the center axis of the tip but displaced therefrom.

31. The insert of claim 30 wherein said passageway is displaced from said axis by about 0.1 to 0.5 mm.

32. The insert of claim 30 wherein the discharge orifice is shaped such that the fluid flowing therefrom forms a desired pattern for contacting dental surfaces contacted by said tip.

33. A method of subgingivially cleaning a tooth, comprising:

contacting a subgingival surface of said tooth adjacent to the gum covering said tooth surface with a transducer activated tool tip having an inlet end and a subgingival outlet end, said subgingival end exending distally from a step in the outer surface of the tip and being shaped to contact said tooth surface, said subgingival outlet end of said tip having a longest cross-sectional dimension of less than 0.03 inch; a passageway wall being offset from the centerline of the tip whereby a discharge orifice is formed by an edge of said passageway wall at a side of said tip, and directing a fluid to said subgingival surface of said tooth and between said subgingival surface of said tooth and the gum in which said tooth is supported.

34. The method of claim 33 wherein said step intersects said passageway wall orifice.

35. The method of claim 33 wherein a line on the outer surface of an outer wall of said tip of said inlet end adjacent to said step forms a first angle with a center axis, a line on the outer surface of said outer wall of said tip of said subgingival end adjacent to said step forms a second angle with said center axis, and said first angle is greater than said second angle.

36. The method of claim 33 wherein a line on the outer surface of an outer wall of said tip of said inlet end adjacent to and within 3 mm of said step forms a first angle with a center axis, a line on the outer surface of said outer wall of said tip of said subgingival end adjacent to and within 3 mm of said step forms said second angle with said center axis, and said lines are at least 0.1 mm apart at said step.

37. The method of claim 33 wherein said step is a shoulder and said fluid discharge orifice intersects said shoulder.

38. A method of making a transducer activated tool tip for contacting subgingival tooth surfaces and directing a fluid adjacent to said surfaces, comprising, shaping a tip body to form distal surfaces for contacting said subgingival tooth surfaces; and forming in said tip body a fluid passageway internal to said tip, said tip having an inlet end and a subgingival outlet end, said subgingival end exending distally from a step in the outer surface of the tip and being shaped to contact said tooth surfaces, said subgingival outlet end of said tip having a longest cross-sectional dimension of less than 0.03 inch; a passageway wall being offset from the centerline of the tip whereby a discharge orifice is formed by an edge of said passageway wall at a side of said tip.

39. The method of claim 38 wherein forming of said fluid passageway comprises electric discharge machining said passageway in a cylindrical rod, beginning at the center axis of an end of said rod and continuing at an angle of less than about 3 degrees from the center axis of said rod such that the passageway forms a discharge orifice 2–8 mm from an opposite, distal end of said rod.

40. The method of claim 39 wherein shaping of said cylindrical rod into a desired shape for contacting subgingival tooth surfaces comprises machining and bending such that a fluid orifice is on a concave surface thereof to direct fluid adjacent or onto said tooth surfaces.

41. The method of claim 38 wherein forming said tip fluid passageway comprises:

securing a cylindrical rod in a lathe such that the tail end of said rod opposite said rod distal surfaces is offset from the longitudinal center axis of the lathe; and boring said rod such that said passageway forms a fluid discharge orifice 2–14 mm from the distal end of said tip.

42. The method of claim 38 wherein said tip further comprises a shoulder and said fluid discharge orifice intersects said shoulder.

* * * * *